US008197411B2

United States Patent
Matsumura

(10) Patent No.: US 8,197,411 B2
(45) Date of Patent: Jun. 12, 2012

(54) REFERENCE DEFORMABLE BODY, ULTRASONIC DIAGNOSTIC APPARATUS, AND ULTRASONIC DIAGNOSTIC METHOD

(75) Inventor: Takeshi Matsumura, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 12/989,514

(22) PCT Filed: Apr. 14, 2009

(86) PCT No.: PCT/JP2009/057469
§ 371 (c)(1),
(2), (4) Date: Oct. 25, 2010

(87) PCT Pub. No.: WO2009/131027
PCT Pub. Date: Oct. 29, 2009

(65) Prior Publication Data
US 2011/0040185 A1   Feb. 17, 2011

(30) Foreign Application Priority Data
Apr. 25, 2008   (JP) .................. 2008-114869

(51) Int. Cl.
*A61B 8/00*   (2006.01)
(52) U.S. Cl. ..................... 600/443; 600/459
(58) Field of Classification Search .............. None
See application file for complete search history.

(56) References Cited

U.S. PATENT DOCUMENTS
| | | | | |
|---|---|---|---|---|
| 4,340,944 A | * | 7/1982 | Dory | 367/96 |
| 6,500,126 B1 | * | 12/2002 | Brock-Fisher | 600/459 |
| 7,242,793 B2 | * | 7/2007 | Trobaugh et al. | 382/128 |
| 7,369,458 B2 | * | 5/2008 | Sifferman et al. | 367/13 |
| 2002/0107538 A1 | * | 8/2002 | Shibata et al. | 606/169 |
| 2005/0096547 A1 | * | 5/2005 | Wendelken et al. | 600/459 |

FOREIGN PATENT DOCUMENTS
| | | | |
|---|---|---|---|
| JP | 3-27214 | | 3/1991 |
| JP | 05-076528 | | 3/1993 |
| JP | 06-154215 | | 6/1994 |
| JP | 07-178089 | | 7/1995 |
| JP | 10014917 A | * | 1/1998 |
| JP | 2003-070788 | | 3/2003 |
| JP | 2005-066041 | | 3/2005 |
| JP | 2007-014485 | | 1/2007 |
| JP | 2007-215672 | | 8/2007 |
| JP | 2007-236823 | | 9/2007 |
| WO | WO 2005/120358 A1 | | 12/2005 |
| WO | WO 2008016022 A1 | * | 2/2008 |

* cited by examiner

*Primary Examiner* — Long V. Le
*Assistant Examiner* — Bo J Peng
(74) *Attorney, Agent, or Firm* — Antonelli, Terry, Stout & Kraus, LLP.

(57) ABSTRACT

An ultrasonic diagnostic apparatus and method are disclosed for enabling identification of a type of reference deformable body. The ultrasonic diagnostic apparatus includes an ultrasonic probe to which the reference deformable body is attached, a tomographic image constructing unit, and a display unit. The ultrasonic diagnostic apparatus further includes a storing unit configured to store the relationship between the ID given to the reference deformable body and a type of the reference deformable body, and a type identifying unit configured to specify the type of the reference deformable body corresponding to the inputted ID. A tomographic image can then be constructed based on the type of reference deformable body specified.

19 Claims, 11 Drawing Sheets

(a)

ID: α (BAR CODE WITH ONE BAR)

(b)

ID: β (BAR CODE WITH TWO BARS)

\* : REFERENCE DEFORMABLE BODY (a) BEFORE CORRECTION (b) AFTER CORRECTION

* : REFERENCE DEFORMABLE BODY

REFERENCE DEFORMABLE BODY, ULTRASONIC DIAGNOSTIC APPARATUS, AND ULTRASONIC DIAGNOSTIC METHOD

FIELD OF THE INVENTION

The present invention relates to a reference deformable body to be attached on an ultrasonic wave transmission/reception surface of an ultrasonic probe, an ultrasonic diagnostic apparatus and ultrasonic diagnostic method for displaying a tomographic image of an imaging target portion in an object to be examined using ultrasonic waves or an elasticity image which presents hardness or softness of biological tissues.

DESCRIPTION OF RELATED ART

An ultrasonic diagnostic apparatus transmits an ultrasonic wave to the inside of an object to be examined using an ultrasonic probe, receives the reflected echo signal of the ultrasonic wave from the inside of the object according to the structure of the biological tissue, and constructs a tomographic image such as a B-mode image to display for diagnosis.

Ultrasonic diagnostic apparatuses of recent years measure an ultrasonic wave receiving signal by pressing an object using an ultrasonic probe manually or mechanically, acquire displacement of the tissues, and display an elasticity image of the biological tissues based on the acquired displacement data. At this time, the method has been disclosed wherein a reference deformable body is attached to the ultrasonic probe via a fixing member, the border between the object and the reference deformable body is detected from the RF signal frame data acquired by transmission and reception of the ultrasonic waves, and the pressure applied to the object is measured from the positional information of the border (for example, Patent Document 1).

PRIOR ART DOCUMENT

Patent Document

Patent Document 1: WO2005/120358

There are various types of reference deformable bodies to be attached to an ultrasonic probe. For example, since there are different sizes or shapes of ultrasonic probes, the size or shape of the reference deformable body best suited to each of those probes would be also different. For a linear-type ultrasonic probe, a linear-type reference deformable body is to be attached. For a convex-type of ultrasonic probe, a curved reference deformable body is to be attached. Also, when depth or size of a measuring portion or physical attribute of the object is different, hardness or thickness of the reference deformable body needs to be changed. In this manner, it is necessary to switch types of the reference deformable body to have optimal feature according to the measurement condition.

However, if the type of the reference deformable body is not identified, elasticity modulus calculation or ultrasonic wave transmission/reception setting cannot be executed properly.

The objective of the present invention is to identify the type of a reference deformable body to be attached to an ultrasonic probe.

SUMMARY OF THE INVENTION

In order to achieve the objective of the present invention, the ultrasonic diagnostic apparatus comprises:

an ultrasonic probe having the ultrasonic wave transmitting/receiving surface on which a reference deformable body is attached;

a tomographic image constructing unit configured to transmit/receive an ultrasonic wave to/from an object to be examined via the reference deformable body, and generate a tomographic image based on the RF signal frame data of the cross-sectional region of the object; and a display unit configured to display the tomographic image, characterized in further comprising:

a storing unit configured to store the relationship between an ID given to the reference deformable body and the type of the reference deformable body; and a type identifying unit configured to read out the type of the reference deformable body corresponding to the ID of the reference deformable body attached to the ultrasonic probe and to identify the type of the reference deformable body. Consequently, the type of the reference deformable body can be identified.

It also comprises an image analyzing unit configured to analyze feature quantity of the reference deformable body in the tomographic image, wherein:

the storing unit stores the relationship between the analyzed feature quantity of the reference deformable body and the type of the reference deformable body; and the type identifying unit reads out the type of the reference deformable body corresponding to the feature quantity of the reference deformable body in the newly-obtained tomographic image, and identifies the type of the reference deformable body. Consequently, the type of the reference deformable body can be identified.

Furthermore, it comprises an image processing means configured to shift a tomographic image or an elasticity image toward the ultrasonic probe side in accordance with the thickness of the reference deformable body identified in the type identifying unit. Furthermore, it comprises an ultrasonic wave transmission/reception control unit configured to control the focus of the ultrasonic wave in accordance with the thickness of the reference deformable body identified by the type identifying unit, so that the ultrasonic wave will not be focused on the reference deformable body.

In the present invention, the type of a reference deformable body can be identified, and the information thereof can be reflected to calculation of elasticity or displayed.

DESCRIPTION OF REFERENCE NUMERALS

1: ultrasonic wave transmission/reception control circuit, 2: transmitting circuit, 3: ultrasonic probe, 4: receiving circuit, 5: phasing and adding circuit, 6: signal processing unit, 7: black and white scan converter, 8: RF signal frame data selecting unit, 9: displacement/strain calculating unit, 10: elasticity modulus calculating unit, 11: elasticity data processing unit, 12: color scan converter, 13: switching and adding unit, 14: image display unit, 15: pressure calculating unit, 16: reference deformable body, 30: reference deformable body information acquiring unit, 32: control unit, 34: input unit, 36: cine memory

DETAILED DESCRIPTION OF THE INVENTION

Figure 1:
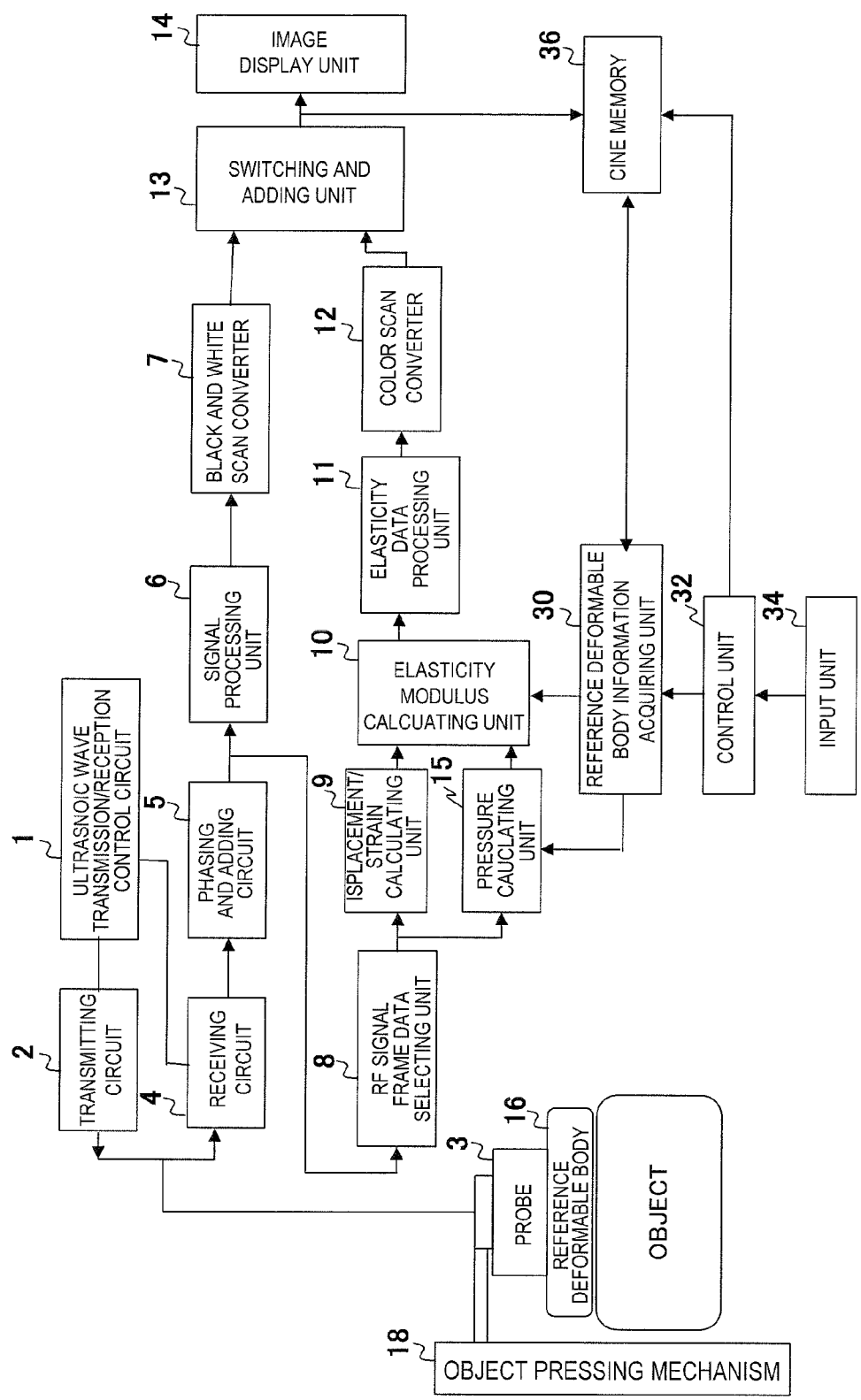
FIG. 1 shows the general configuration of the present invention.

An embodiment of the present invention will be described referring to the diagrams. FIG. 1 shows a block diagram of the ultrasonic diagnostic apparatus related to the present invention. An ultrasonic diagnostic apparatus is for acquiring a tomographic image of a measuring portion in an object to be examined using ultrasonic waves and displaying an elasticity image that presents hardness or softness of biological tissues.

The ultrasonic diagnostic apparatus is Configured comprising ultrasonic wave transmission/reception control circuit 1, transmitting circuit 2, ultrasonic probe 3, receiving circuit 4, phasing and adding circuit 5, signal processing unit 6, black and white scan converter 7, RF signal frame data selecting unit 8, displacement/strain calculating unit 9, elasticity modulus calculating unit 10, elasticity data processing unit 11, color scan converter 12, switching and adding unit 13, image display unit 14, pressure calculating unit 15, reference deformable body 16, reference deformable body information acquiring unit 30, control unit 32, input unit 34 and cine memory 36 as shown in FIG. 1.

Ultrasonic probe 3 is formed by disposing multiple strips of transducers therein, for transmitting and receiving ultrasonic waves to/from an object by scanning beams mechanically or electronically. Each transducer generally has the function that converts incoming pulse waves or continuous transmitting signals into ultrasonic waves and discharges the converted ultrasonic waves, and the function that converts the reflected echoes discharged from inside of the object into electronic signals (reflected echo signals) and outputs the converted signals.

Reference deformable body 16 is attached on the ultrasonic wave transmitting/receiving surface of ultrasonic probe 3. Reference deformable body 16 is to be applied on the body surface of the object to give compression. Compressing motion renders transmission/reception of ultrasonic waves via ultrasonic probe, and provides stress distribution to the measuring portion in the body cavity.

Ultrasonic wave transmission/reception control circuit 1 controls the timing or focus for transmitting and receiving ultrasonic waves. Transmitting circuit 2 produces transmission pulses for generating ultrasonic waves by driving ultrasonic probe 3, and sets the convergent point (focus) of the ultrasonic waves transmitted by an internal transmission phasing and adding circuit at a certain depth. Receiving circuit 4 amplifies the reflected echo signal received by ultrasonic probe 3 at a predetermined gain. The number of reflected echo signals which corresponds to the number of the amplified respective transducers is inputted to phasing and adding circuit 5. Phasing and adding circuit 5 controls the phase of the reflected echo signal amplified in receiving circuit 4, and forms RF signal frame data.

Signal processing unit 6 and black and white scan converter 7 are provided on one end of the output side of phasing and adding circuit 5. Signal processing unit 6 inputs the RF signal frame data from phasing and adding circuit 5, and executes various signal processing such as gain compensation, log compensation, detection, edge enhancement and filtering.

Black and white scan converter 7 obtains the RF signal frame data signal processed in signal processing unit 6 at a predetermined cycle, and reads out the tomographic image data based on the RF signal frame data at TV system cycle.

Also, RF signal frame data selecting unit 8, displacement/strain calculating unit 9, pressure calculating unit 15 and elasticity modulus calculating unit 10 are comprised on the output side of the other end of phasing and adding circuit 5. Also, elasticity data processing unit 11 and color scan converter 12 are comprised on the latter part of elasticity modulus calculating unit 10.

On the output side of black and white scan converter 7 and color scan converter 12, switching and adding unit 13 is comprised. Image display unit 14 is a monitor for displaying a tomographic image based on the tomographic image data obtained by black and white converter 7 and an elasticity image based on the elasticity image data obtained by the color scan converter. Cine memory 36 on the output side of switching and adding unit 13 is for storing tomographic image data and elasticity image data with time information. The tomographic image data and elasticity image data stored in cine memory 36 are displayed on image display unit 14 according to the command from input unit 34.

RF signal frame data selecting 8 sequentially stores the RF signal frame data outputted from phasing and adding circuit 5 (the currently stored RF signal frame data is set as RF signal frame data N) in the frame memory provided in RF frame data selecting unit 8, selects one set of RF signal frame data from among the past RF signal frame data N−1, N−2, N−3, . . . N−M (the selected data is set as RF signal frame data X), and outputs a pair of RF signal frame data N and RF signal frame data X to displacement/strain calculating unit 9. While RF signal frame data is described above as the signal to be outputted from phasing and adding circuit 5, it may also be the form of I,Q signal which is the complex-demodulated RF signal.

Displacement/strain calculating unit 9 executes one-dimensional or two-dimensional correlationship process based on the pair of RF signal frame data selected by RF signal frame data selecting unit 8, measures displacement or moving vector (direction and size of displacement) of the respective measurement points on a tomographic image, generates displacement frame data, and calculates the strain from the generated strain frame data. The strain is to be calculated, for example, by performing spatial differentiation on the displacement. The moving vector is to be detected, for example, using the block matching method or the gradient method. Block matching method divides an image into blocks formed by, for example, N×N pixels, searches the block which is most approximated to the target block in the current frame from the previous frame, and performs encoding referring to the searched blocks.

Elasticity modulus calculating unit 10 calculates elasticity modulus from the strain information outputted from displacement/strain calculating unit 9 and from the pressure information outputted from pressure calculating unit 15, generates numerical data of the elasticity modulus (elasticity frame data), and outputs the generated data to elasticity data processing unit 11 and color scan converter 12. One of elasticity modulus, for example, Young's modulus Ym is to be obtained by dividing the stress (pressure) in each calculation point by the strain in each calculation point, as shown in the equation below. In the equation below, the index of i,j represents the coordinate of the frame data.

$$Ym_{i,j} = \text{pressure(stress)}_{i,j}/(\text{strain } i,j)(i,j=1, 2, 3 \ldots) \quad \text{[Equation 1]}$$

Here, the pressure given to the object is measured in pressure measuring unit 15. Pressure measuring unit 15 obtains the pressure given to reference deformable body 16 by calculation, and outputs it as the pressure given to the object. The detail on this step will be described later.

Elasticity data processing unit 11 executes various image processing such as smoothing process in the coordinate plane of the calculated elasticity frame data, contrast optimization process, or smoothing process among the frames in the time axis direction.

Color scan converter 12 provides color information on light's three primary colors that are red(R), green(G) and blue(B) to the elasticity frame data outputted from elasticity data processing unit 11. For example, large elasticity modulus is converted into red color code, and small elasticity modulus is converted into blue color code.

Also, object pressing mechanism 18 moves ultrasonic probe 3 in vertical directions using a device such as motor or wire so as to press the object, or an operator may manually move ultrasonic probe 3 in vertical direction.

First Embodiment

Manual Input of ID

Here, the first embodiment will be described referring to FIGS. 1~5. In the first embodiment, an operator inputs an ID to make an ultrasonic diagnostic apparatus to identify the type of a reference deformable body, for reflecting the type to elasticity calculation or displaying the type. This ID is to be the index for identifying the type of the reference deformable body.

The ultrasonic diagnostic apparatus of the first embodiment mainly comprises input unit 34 configured to input an ID of reference deformable body 16, control unit 32 configured to make the ID inputted by input unit 34 to be outputted to reference deformable body information acquiring unit 30, reference deformable information acquiring unit 30 configured to acquire the type of reference deformable body 16 corresponding to the outputted ID and to reflect the type of reference deformable body 16 to calculation in pressure calculating unit 15 or elasticity modulus calculating unit 10.

Figure 2:
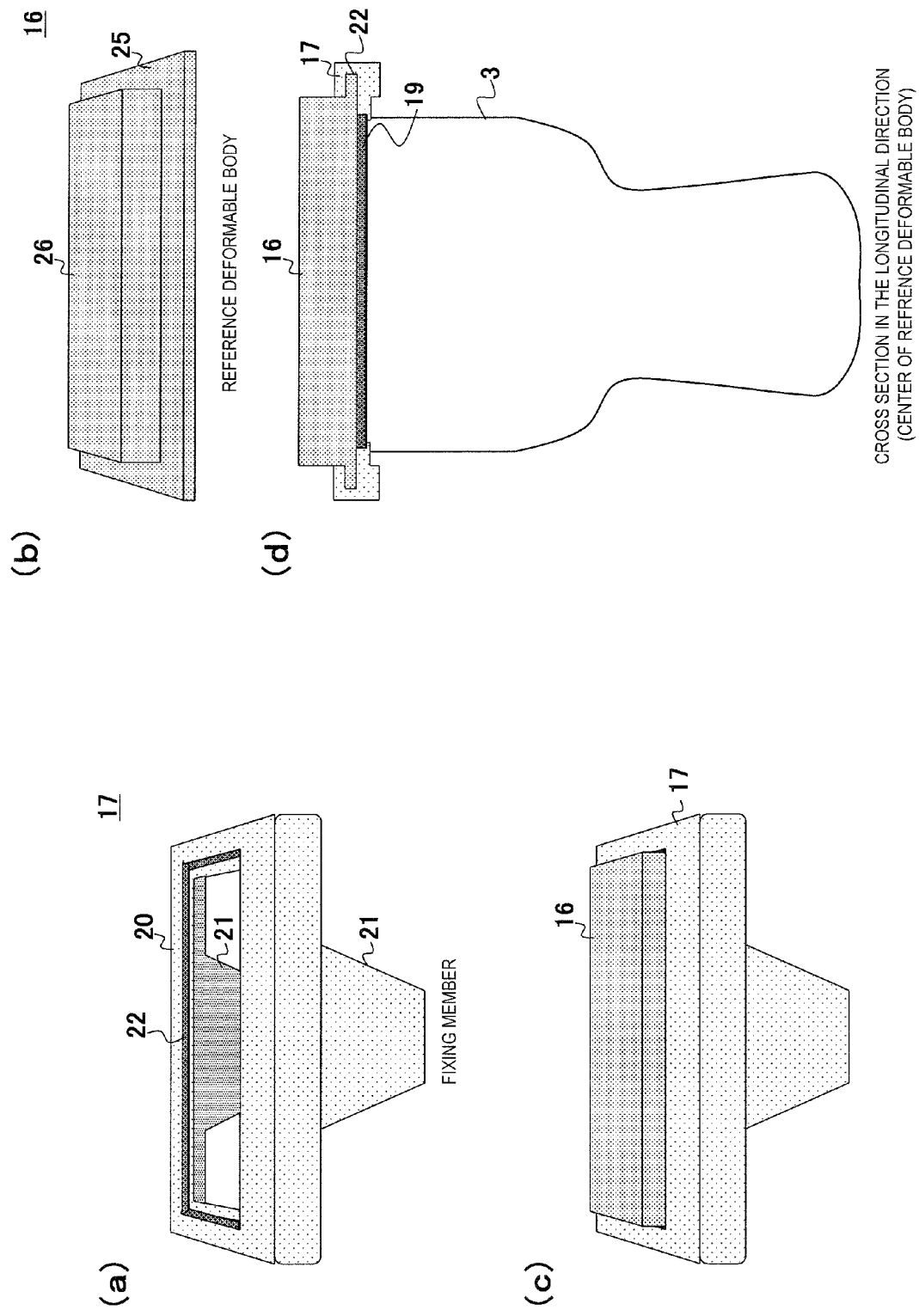
FIG. 2 shows the attachment pattern of a reference deformable body related to the present invention.

First, attachment pattern of reference deformable body 16 will be described using FIG. 2. As shown in FIG. 2(a), fixing member 17 is formed by frame body 20 having airspace in the center thereof and a pair of holding units 21 extended downward from the bottom surface of frame body 20. Frame body 20 and holding units 21 are formed being integrated with each other. On holding unit 21, a protruded portion is provided so as to fit in the slot on the side portion of ultrasonic probe 3 (not illustrated in the diagram). Accordingly, fixing member 17 can be mounted to ultrasonic probe 3 through one-touch operation. Also, on the inner-peripheral surface of the airspace in frame body 20, slot portion 22 is provided for holding reference deformable body 16. The width of lot portion 22 is about 3 mm, and the depth thereof is about 5 mm.

As shown in FIG. 2(b), reference deformable body 16 has a form wherein rectangle body 26 is provided to the central portion on the upper surface of a square-shaped flat-plate body 25. Rectangle body 26 of reference deformable body 16 has the size which can be protruded from the airspace in fixing member 17. Also, flat-plate body 25 has about 3 mm of thickness which can be fit in slot portion 22 of fixing member 17.

Reference deformable body 16 is formed based on oil-based gel material, water-based gel material such as acrylamide or silicon, etc. Acrylamide is formed as acrylamide gel wherein cross-linking agent (BIS) is polymerized in the presence of catalytic agent. This is polymer gel having 3-dimensional meshed structure, and has texture like agar or gelatin. In this manner, the material that is a liquid solution and gets coagulated over time into a gel after coagulating agent is mixed in is preferable for reference deformable body 16. If it is constituted by the material such as acrylamide having low viscosity, it is suited for pressure measurement since it responds to pressing operation quickly. Also, reference deformable body 16 may also be formed by a material based on aqueous resin gelled substance which is to be used as a phantom for diagnosis using ultrasonic waves.

FIG. 2(c) shows a pattern wherein reference deformable body 16 is attached to fixing member 17. The end portion of flat-plate body 25 is inserted into slot portion 22 formed on the inner-peripheral surface of frame body 20, and reference deformable body 16 is attached to fixing member 17. Since flat-plate body 25 which is reference deformable body 16 is an elastic body, flat-plate body 25 can be mounted in slot portion using the elasticity. Accordingly, when reference deformable body 16 is attached to fixing member 17, rectangle body 26 of reference deformable body 16 is protruded from frame body 20 of fixing member 17.

FIG. 2(d) shows the cross-sectional view in the longitudinal direction of the condition that reference deformable body 16 and fixing member 17 are fixed on ultrasonic probe 3. In the condition that reference deformable body 16 is attached to fixing member 17 as shown in FIG. 2(c), fixing member 17 is fixed on ultrasonic probe 3 via holding unit 22. When fixing member 17 is fixed on ultrasonic probe 3, reference deformable body 16 comes to contact transducers 19 provided on the upper part of ultrasonic probe 3. In this condition, the upper surface of reference deformable body 16 is applied to an object, and executes transmission/reception of ultrasonic waves from/to transducers 19.

Figure 3:
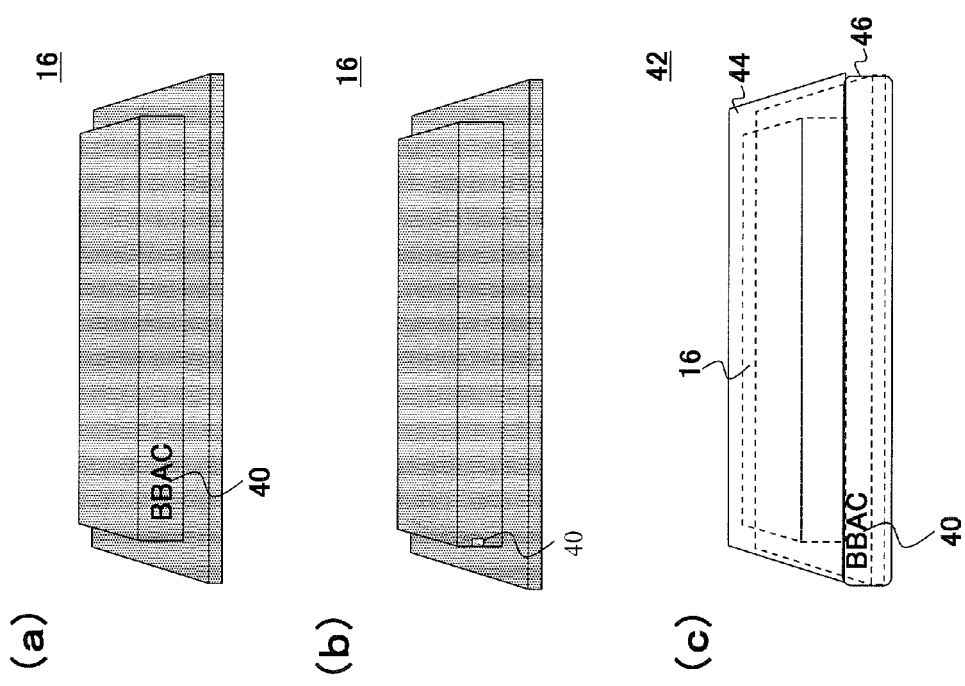
FIG. 3 shows the display pattern of an ID related to the present invention.

Also, as shown in FIG. 3, reference deformable body 16 or package 40 of reference deformable body 16 has ID 40.

(1-1: ID on a Reference Deformable Body)

Concretely, as shown in FIG. 3(a), ID 40 formed by letters is appended on the side surface of reference deformable body 16. ID 40 is, for example, "BBAC" formed by four alphabetical letters. ID 40 is appended on the side surface (the part which does not contact the object) of reference deformable body 16 to avoid the influence thereof in transmission and reception of ultrasonic waves to/from the object. An operator can identify ID 40 by the order of alphabetical letters through checking ID 40 on the side surface of reference deformable body 16. ID 40 may be presented also by numbers, symbols, figures, colors, and so on.

Also, as shown in FIG. 3(b), by providing concavity and convexity for imprinting ID 40 in advance on a metal mold to form reference deformable body 16 and inpouring gel material of reference deformable body in the metal mold, ID 40 formed by concavity and convexity can be formed on the side surface of reference deformable body 16. The operator can identify ID 40 by seeing or touching the concavity and convexity of ID 40 formed on the side surface of reference deformable body 16. Also, surface treatment such as sawtooth or wave pattern may be worked on the side surface of reference deformable body 16.

Also, ID 40 may be identified by dyeing reference deformable body 16. For example, if reference deformable body 16 is white ID 40 is set as "BBAC", and if reference deformable body 16 is yellow ID 40 is set as "AAAA".

(1-2: ID on a Package)

As shown in FIG. 3(c), ID 40 may be appended on case 42 which is for packaging reference deformable body 16. Case 42 has case part 46 having airspace therein and cover part 44, and reference deformable body 16 is contained and sealed between case part 46 and cover part 44. By sealing and containing reference deformable body 16 inside of case 42, deterioration of reference deformable body 16 can be minimized by keeping out dust or air.

The operator can identify the alphabetical letters, i.e. ID 40 of reference deformable body by seeing ID 40 on the case for packaging reference deformable body 16.

(1-3: Manual Input of ID)

Figure 4:
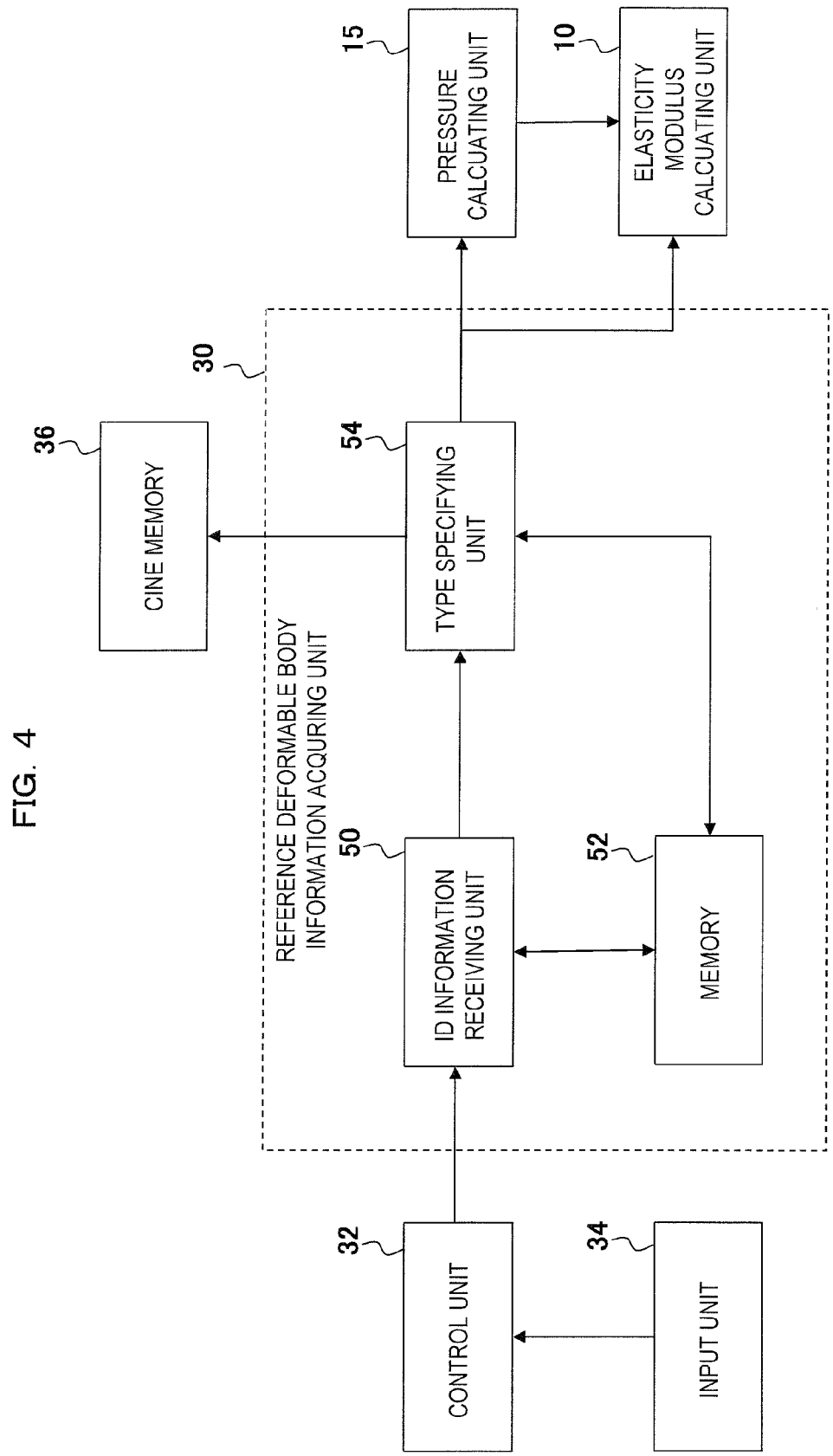
FIG. 4 shows the first embodiment of the present invention.

Next, as shown in FIG. 4, the operator inputs ID 40 of reference deformable body 16 or ID 40 described on case 42 for containing reference deformable body 16 to input unit 34. Control unit 32 outputs ID 40 inputted by input unit 34 to reference deformable body information acquiring unit 30, and gives a command to identify the type of reference deformable body 16. Then reference deformable body information acquiring unit 30 identifies the type of reference deformable body 16 from the outputted ID 40, and reflects the type of reference deformable body 16 to calculation to be executed by pressure calculating unit 16 and elasticity modulus calculating unit 10. Also, reference deformable body information acquiring unit 30 displays the type of reference deformable body 16 on image display unit 14.

In concrete terms, reference deformable body information acquiring unit 30 is formed by ID information receiving unit 50 for receiving the inputted ID 40 of reference deformable body 16, memory 52 for storing a plurality of relationships between IDs 40 of reference deformable body 16 and types of reference deformable body 16 in advance, and type identifying unit 54 for identifying the type of reference deformable body 16 corresponding to the inputted ID 40 based on the information stored in memory 52. Also, in memory 52, one type of reference deformable body (such as thickness, elasticity characteristic, acoustic characteristic and type of the probe) is stored corresponding to one ID 40 as shown in chart 1 below.

CHART 1

| ID | Thickness (mm) | Elasticity characteristics (N/m) | Acoustic characteristics (N · s/m³) | Kind of probe (Applying part) |
|---|---|---|---|---|
| AAAA | 8 | 100 | $1.5 \times 10^6$ | Linear type |
| BAAA | 7 | 100 | $1.5 \times 10^6$ | Linear type |
| BBAA | 7 | 50 | $1.5 \times 10^6$ | Linear type |
| . | . | . | . | . |
| . | . | . | . | . |
| . | . | . | . | . |
| DDDD | 5 | 30 | $1.0 \times 10^6$ | Intracavitary type |

Here, the thickness of reference deformable body 16 is the thickness of reference deformable body in the transmitting/receiving direction of ultrasonic waves, and is the initial thickness before applying pressure. Elasticity characteristics indicate elasticity modulus, viscoelasticity modulus, nonlinearity, Poisson's ratio, etc. of reference deformable body 16. In the present embodiment, elasticity modulus is used as elasticity characteristic. Also, acoustic characteristics indicate acoustic velocity, rate of decrease, acoustic impedance, etc. of reference deformable body 16. In the present embodiment, acoustic impedance is used as acoustic characteristic. The type of probe indicates the type of ultrasonic probe 3 to which reference deformable body 16 is attached. For example, there are different types such as linear type of ultrasonic probe 3 for pressing from outside of the body or a convex type of ultrasonic probe 3, or an intracavitary type of ultrasonic probe 3 for pressing from inside of the object's body, and the applying part is to be determined.

The four alphabetical letters which indicate ID 40 respectively correspond to the type of each reference deformable body 16. The far-left alphabet corresponds to the thickness of each reference deformable body 16. For example, if the far left alphabet is A, it means that the thickness of the reference deformable body is 8 mm, B indicates that the thickness of the reference deformable body is 7 mm, C indicates that the thickness of the reference deformable body is 6 mm, and D indicates that the thickness of the reference deformable body is 5 mm. In this manner, the operator can recognize the thickness of reference deformable body 16 by only looking at ID 40. In the same manner, the second left alphabet corresponds to the elasticity characteristics. The third left alphabet corresponds to the acoustic characteristic, and the far-right alphabet corresponds to the type of ultrasonic probe to which reference deformable body 16 is attached.

Then kind identifying unit 54 identifies the kind of reference deformable body 16 corresponding to the inputted ID 40 by reading it out from memory 52. Input unit 34 may also input the information on characteristics (for example, elasticity characteristics, etc. of reference deformable body 16) of reference deformable body 16 instead of ID 40.

(1-4: Pressure Measurement)

Type identifying unit 54 outputs the type of reference deformable body 16 to pressure calculating unit 15. Pressure calculating unit 15 detects the thickness and the elasticity modulus in particular from among the types of reference deformable body 16 (thickness, elasticity characteristics, acoustic characteristics, type of probe, etc.) outputted from reference deformable body information acquiring unit 30. The detected thickness is the initial thickness of reference deformable body 16 before pressure is applied to the object.

Pressure calculating unit 15 obtains the strain of reference deformable body 16 deformed by the pressure applied to the object, from the RF signal frame data outputted from RF signal frame data selecting unit 8. In concrete terms, pressure calculating unit 15 first extracts the RF signal frame data in the region including the border between the object and reference deformable body 16. Then it obtains the coordinate of the border between the object and reference deformable body 16 based on the extracted RF signal frame data. For example, the threshold value is set with respect to the amplitude of the signal wave pattern of the RF signal frame data including the border, the threshold value is set as original point 0 in the depth direction (contact plane of the transducer and reference deformable body 16), and the coordinate wherein the amplitude of the waveform of the RF signal frame data first surpasses the threshold value from in the depth direction from the original point is detected as the coordinate of the border.

Figure 5:
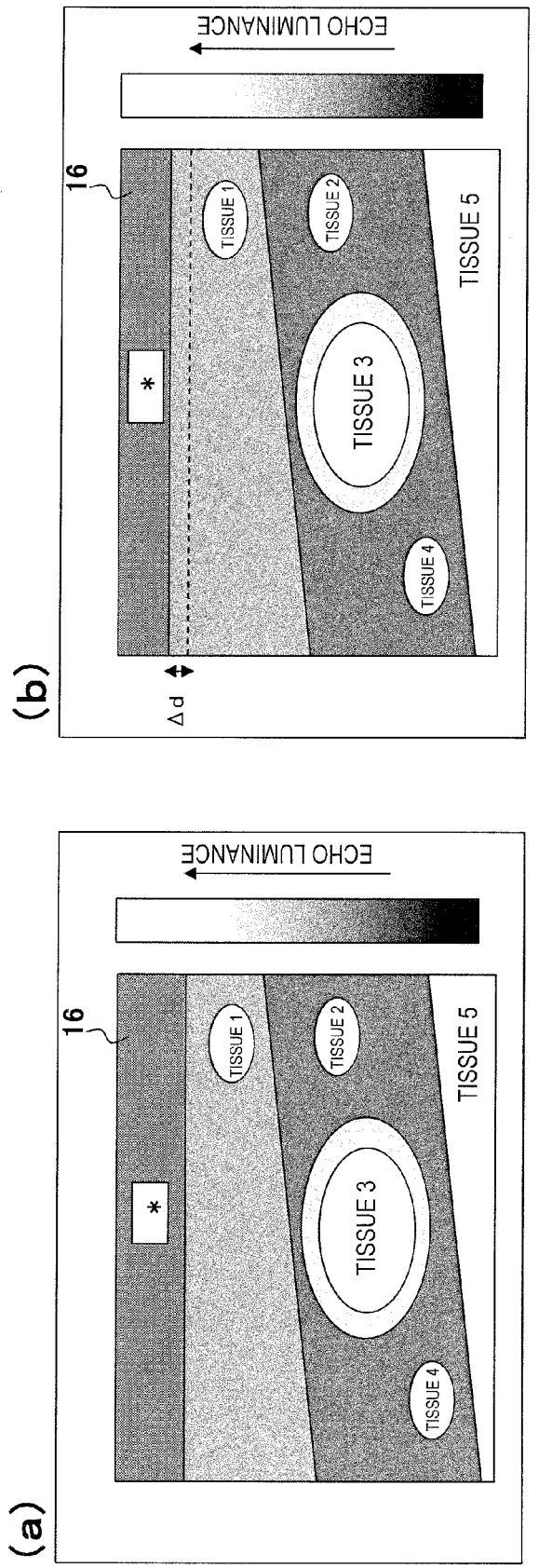
FIG. 5 shows an embodiment of pressure measurement related to the present invention.
Figure 6:
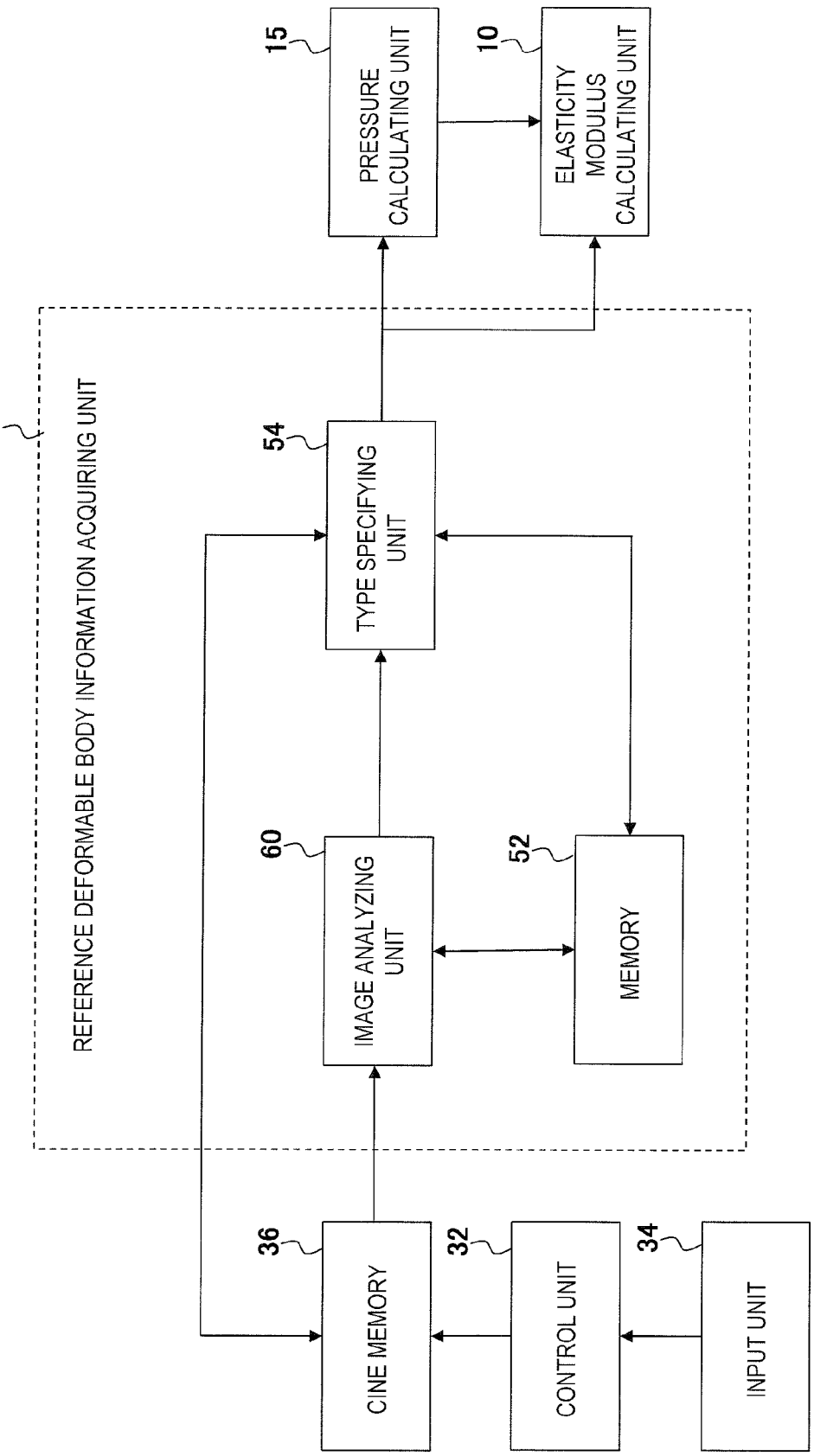
FIG. 6 shows the second embodiment of the present invention.

While the border between the object and reference deformable body 16 is detected above based on the RF signal frame data, the tomographic image data outputted from black and white scan converter 16 may also be used for detecting the border. FIG. 5(a) shows the condition of reference deformable body 16 before pressure is applied on the object. FIG. 5(*b*) shows the condition of reference deformable body 16 after pressure is applied on the object. Pressure calculating unit 15 detects the coordinate of the border in the tomographic image based on the difference of the acoustic characteristics (acoustic velocity, rate of decrease and acoustic impedance) between tissue 1 and reference deformable body 16.

Then pressure calculating unit 15 associates the initial thickness of reference deformable body 16 before pressure is applied with the coordinate of the border. Also, pressure calculating unit 15 calculates the displacement of reference deformable body 16 from the coordinate of the border after pressure is applied, based on the association between the initial thickness and the coordinate of the border. Pressure calculating unit 15 then calculates the strain from the calculated displacement and the initial thickness.

Also, elasticity modulus (a part of elasticity characteristics) of reference deformable body 16 is identified by type identifying unit 54 based on ID 40. Consequently, by setting P as (pressure(stress)), Y as (elasticity modulus) and δd as (strain), their relationship can be expressed by the following equation.

$$P(\text{pressure(stress)}) = Y(\text{elasticity modulus}) \times \delta d(\text{strain}) \quad \text{[Equation 2]}$$

Pressure calculating unit 15 can obtain the pressure in the border between the object and reference deformable body 16 based on the above-mentioned equation 2.

(1-5: Calculation of Elasticity Modulus)

Elasticity modulus calculating unit 10 calculates elasticity modulus based on the above equation 1 from the strain information outputted from displacement/strain calculating unit 9 and the pressure information outputted from pressure calculating unit 15, and generates numerical data (elasticity frame data) of the elasticity modulus. Elasticity modulus calculating unit 10 outputs the elasticity frame data to elasticity data processing unit 11.

Color scan converter 12 appends hue information to the elasticity frame data outputted from elasticity data processing unit 11, and image display unit 14 displays the elasticity image based on the elasticity image data acquired by the color scan converter. Though not shown in the diagram, image display unit 14 may also display the elasticity modulus outputted from elasticity modulus calculating unit 10 by numerical values.

As described above, in accordance with the present embodiment, it is possible to identify the type of reference deformable body 16 by ID 40, and to reflect the identified information on elasticity calculation, whereby calculation of elasticity can be more stable.

(1-6: ID Display)

Also, type identifying unit 54 outputs the type of reference deformable body 16 or ID 40 to cine memory 36. Cine memory 36 stores the type of reference deformable body 16 or the information on ID 40 along with the elasticity image or tomographic image. Image display unit 14 outputs the type of reference deformable body 16 or the information on ID 40 along with the elasticity image or tomographic image from cine memory 36 and displays them. In this manner, the type of the reference deformable body or ID 40 can be displayed.

The operator can execute the setting of ultrasonic waves properly since the type of reference deformable body 16 or ID 40 can be identified. Also, after performing the ultrasonic diagnosis, he/she can identify which type of reference deformable body was used for obtaining the elasticity image or tomographic image upon reviewing the elasticity image or tomographic image obtained by applying reference deformable body 16.

Also, dedicated information on ultrasonic probe 3 is appended to ID 40 as shown in chart 1. Though not shown in the diagram, it is possible to set the procedure to display the warning or to make sounds when reference deformable body 16 is applied to a nondedicated ultrasonic probe 3 and transmission/reception of ultrasonic waves is executed.

Second Embodiment

ID Automatic Identification (2-1: Echo Luminance)

Here, the second embodiment will be described using FIG. 6~FIG. 9. The difference from the first embodiment is that ID 40 of reference deformable body 16 is automatically identified.

Reference deformable body information identifying unit 30 is formed by image analyzing unit 60 configured to the tomographic image stored in cine memory 36, memory 52 configured to store the relationship between a plurality of IDs 40 of reference deformable body 16 and feature quantity of the tomographic image of reference deformable body 16 in advance, and type identifying unit 54 configured to identify the type of reference deformable body 16 corresponding to the inputted tomographic image based on the information stored in memory 52.

Reference deformable body 16 includes, for example, a scatterer. Image analyzing unit 60 analyses the echo luminance in the tomographic image of reference deformable body 16 in which the scatterer outputted from cine memory 36 is included. The memory 52 stores plural echo luminance (0~255) of reference deformable body 16 by associating them with ID 40 respectively. For example, as shown in chart 2, it is assumed that there are two kinds (ID 40: α,β) of reference deformable bodies 16 having different elasticity modulus or scatterer concentration that are stored in memory 52. It is also assumed that the ultrasonic waves are transmitted/received to/from the respective reference deformable bodies 16 in the same condition.

CHART 2

| ID | Elasticity modulus (kPa) | Scatterer concentration (%) | Echo luminance (0~255) | Thickness (mm) |
| --- | --- | --- | --- | --- |
| α | 10 | 1 | 50 | 8 |
| β | 20 | 3 | 100 | 7 |

Figure 7:
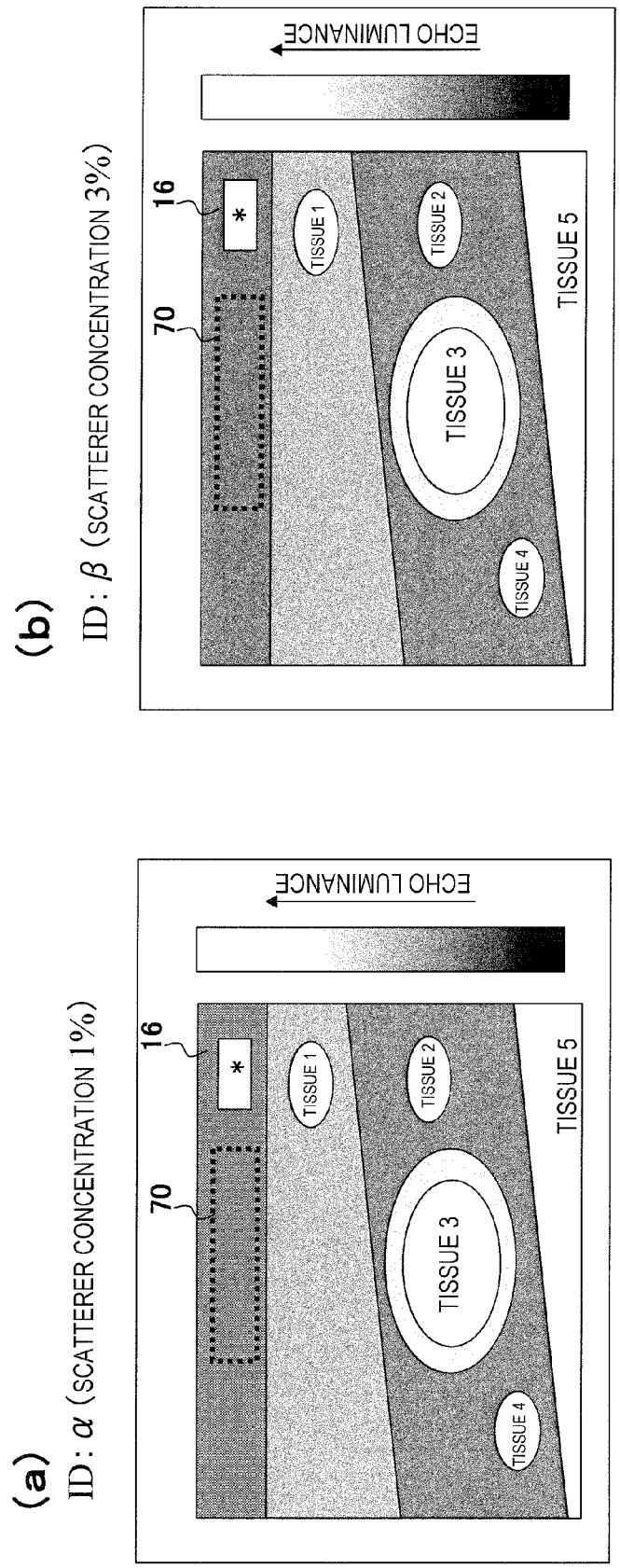
FIG. 7 shows a tomographic image of a reference deformable body in which scatterer is included, which is related to the present invention.

FIG. 7 are tomographic images in the case that reference deformable body 16 (α,β) in which scatterer is included is attached. FIG. 7(*a*) is a tomographic image in the case that reference deformable body 16 having α as ID 40 is attached, and FIG. 7(*b*) is a tomographic image in the case reference deformable body 16 having β as ID 40 is attached.

The echo luminance of reference deformable body 16 is displayed in the region where is shallow in depth (for example, 0~5 mm) in the tomogaphic image. Image analyzing unit 60 analyzes the echo luminance in the shallow region of the tomographic image stored in cine memory 36. For example, image analyzing unit 60 sets ROI 70 in reference deformable body 16 of the tomographic image, and analyzes the luminance information in ROI 70. This ROI 70 is set via input unit 34 as one chooses. Also, it may be set so that ROI 70 is automatically set in the region which is shallow in depth (for example, 0~5 mm) in the tomographic image.

Image analyzing unit 60 analyzes statistical characteristics of the echo luminance such as the average value or dispersion value of the echo luminance in ROI 70. Then type identifying unit 54 reads out the type of reference deformable body 16 corresponding to the characteristics of the echo luminance in the analyzed tomographic image from memory 52 and identifies it.

In concrete terms, if the average value of the echo luminance in ROI 70 is "50", type identifying unit 54 identifies that ID 40 of reference deformable 16 is α. Also, if the average value of the echo luminance in ROI 70 is "100", type identifying unit 54 identifies that ID 40 of the reference deformable body is β.

Then type identifying unit 54 outputs the type (here, elasticity modulus, scatterer concentration, echo luminance and thickness) or ID 40 of reference deformable body 16 to cine memory 36. Cine memory 36 stores the information on the type or ID 40 of reference deformable body 16 along with the elasticity image or tomographic image. Image display unit 14 outputs the information on the type or ID 40 of reference deformable body 16 along with the elasticity image or tomographic image from cine memory 36, and displays them. Accordingly, the operator can identify the type or ID 40 of reference deformable body, and set ultrasonic waves appropriately. Also, he/she can identify the type of reference deformable body 16 used for obtaining the elasticity image or tomographic image.

Also, as in the same manner as the first embodiment, elasticity modulus may be calculated based on the type of reference deformable body 16. Type identifying unit 54 outputs the type of reference deformable body 16 to pressure calculating unit 15, and pressure calculating unit 15 calculates the pressure. Then elasticity modulus calculating unit 10 calculates elasticity modulus from the strain information outputted from displacement/strain calculating unit 9 and the pressure information outputted from pressure calculating unit 15, and generates the numerical data (elasticity frame data) of the elasticity modulus. Image display unit 14 displays the elasticity image or elasticity modulus based on the generated elasticity frame data.

(2-2: Attenuation Characteristics)

While the type of reference deformable body 16 is identified above from the average value of the echo luminance in reference deformable body 16, there are cases, for example, that approximately average echo luminance is distributed even when the scatterer concentration of reference deformable body 16 is greatly different.

Given this factor, type identifying unit 54 may identify the type of reference deformable body 16 from attenuation characteristic of reference deformable body 16. Attenuation characteristic is the feature that ultrasonic waves attenuate in proportion to the scatterer concentration. Image analyzing unit 60 analyzes the attenuation characteristics from distribution of the intensity of echo luminance in reference deformable body 16. The intensity of echo luminance in reference deformable body 16 has the characteristic that it attenuates as moving from the shallow depth portion to the deep portion.

When the ultrasonic waves having low transmitting voltage are transmitted/received to/from ultrasonic probe 3 and the scatterer concentration of reference deformable body 16 is high, attenuation rate is great and the intensity of echo luminance attenuates drastically. ID 40 in this condition is set as α. Also, when the ultrasonic waves having high transmitting voltage are transmitted/received to/from ultrasonic probe 3 and the scatterer concentration is low, attenuation rate is small and the intensity of echo luminance attenuates gradually. ID 40 of this reference deformable body 16 is set as β. The relationship between the attenuation of reference deformable body 16 and ID 40 is stored in memory 52.

Image analyzing unit 60 analyzes the attenuation rate from the distribution of the intensity in echo luminance of the scatterer in ROI 70. Then type identifying unit 54 reads out and identifies the type of reference deformable body 16 corresponding to the attenuation rate from memory 52. Type identifying unit 54, in the case that the attenuation rate in ROI 70 is high, identifies that ID 40 of reference deformable body 16 is α. In the case that the attenuation rate in ROI is low, it identifies that ID 40 of reference deformable body 16 is β.

(2-3: Pattern of Scatterer)

Also, type identifying unit 54 may identify the type of reference deformable body 16 from density distribution (rarefaction density) of scatterer in reference deformable body 16.

For example, in the case that density distribution of the scatterer of reference deformable body 16 gets higher as it moves from the shallow region to the deep region, ID 40 of reference deformable body 16 is set as α. In the case that the density distribution of the scatterer of reference deformable body 16 gets lower as it moves from the shallow region to the deep region, ID 40 of reference deformable body 16 is set as β. The relationship between the scatterer distribution of reference deformable body 16 and ID 40 is to be stored in memory 52.

Image analyzing unit 60 analyzes density distribution of the scatterer from the echo luminance in ROI 70. Then type identifying unit 54 reads out and identifies the type of reference deformable body 16 corresponding to the density distribution of the analyzed scatterer from memory 52.

Type identifying unit 54, in the case that the echo luminance in ROI 70 gets lower as it moves from the shallow region to the deep region, identifies that ID 40 of reference deformable body 16 is α. Type identifying unit 54, in the case that the echo luminance in ROI 70 gets higher as it moves from the shallow region to the deep region, identifies that ID 40 of reference deformable body 16 is β. Type identifying unit 54 may also identify the type of reference deformable body 16 based on discreteness (dispersion in normal distribution) of the echo luminance distribution in the scatterer of reference deformable body 16.

(2-4: Size and Form of Scatterer)

Also, deformable body type identifying unit 54 may identify the type of reference deformable body 16 from the size of the scatterer. For example, when the size of the scatterer included in reference deformable body 16 is 5 μm, ID 40 of reference deformable body 16 is set as α. When the size of the scatterer included in reference deformable body 16 is 10 μm, ID 40 of reference deformable body is set as β. At this time, it is to be assumed that a plurality of scatterers having even size are included in reference deformable body 16. The relationship between the size of the scatterer in reference deformable body 16 and ID 40 is stored in memory 52.

Image analyzing unit 60 analyzes the size of the scatterer from echo luminance in ROI 70. Then type identifying unit 54 reads out and identifies the type of reference deformable body 16 corresponding to the size (5 μm or 10 μm) of the analyzed scatterer. Also, deformable body type identifying unit 54 can also identify the form of the scatterer in reference deformable body 16 using the pattern matching method. It is set so that the form of the scatterer is different for each ID 40 of reference deformable body 16.

The relationship between the form of the scatterer of reference deformable body and ID 40 is stored in memory 52. Image analyzing unit 60 analyzes the form of the scatterer from the echo luminance in ROI 70. Then type specifying unit 54 executes the pattern matching method between the form of the scatterer stored in memory 54 and the form of the analyzed scatterer. Type identifying unit 54 reads out and identifies the type of reference deformable body 16 including the best matched scatterer stored in the memory.

(2-5: Layer and Barcode)

Figure 8:
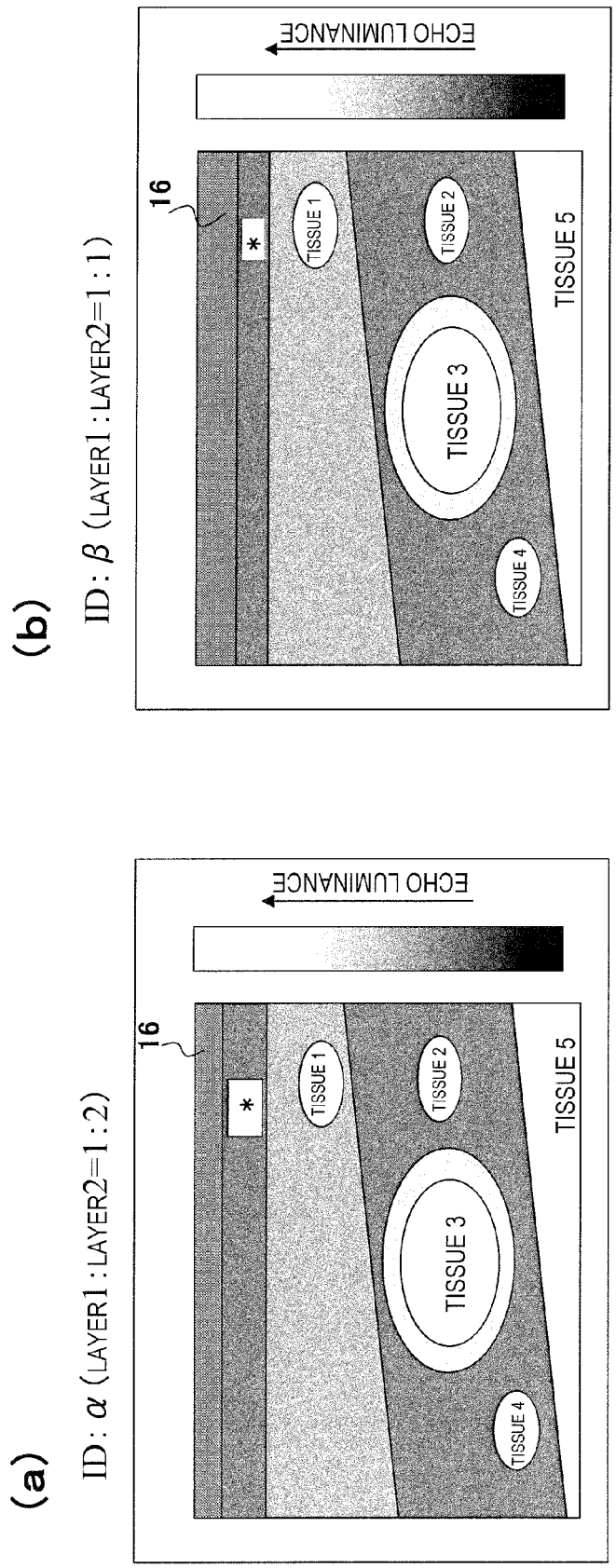
FIG. 8 shows a tomographic image of a reference deformable body formed by a plurality of different layers, which is related to the present invention.

Also, deformable body type identifying unit 54 may identify the type by the pattern or barcode of reference deformable body 16. As shown in FIG. 8, reference deformable body 16 is assumed to be formed by a plurality of different kinds of layers (layer 1 and layer 2). Layer 1 is on the side of ultrasonic probe 3, and layer 2 is on the side of the object.

As shown in FIG. 8(*a*), in the case that the ratio between layer 1 and layer 2 of reference deformable body 16 is (layer 1:layer 2=1:2), ID 40 of reference deformable body 16 is set as α. As shown in FIG. 8(*b*), in the case that the ratio thereof is (layer 1:layer 2=1:1), ID 40 of reference deformable body is set as β. The relationship between the ratio between the layers of reference deformable body 16 and ID 40 is stored in memory 52.

Image analyzing unit 60 analyzes the ratio between layer 1 and layer 2 of reference deformable body 16 from the echo luminance of an elasticity image. In concrete terms, image analyzing unit 60 detects the border between layer 1 and layer 2, and the border between layer 2 and tissue 1 based on the echo luminance. Then image analyzing unit 60 detects the height of layer 1 and layer 2 in the depth direction from the respective borders. Type identifying unit 54 then reads out and identifies ID 40 of reference deformable body 16 corresponding to the detected ratio between layer 1 and layer 2 from memory 52.

Figure 9:
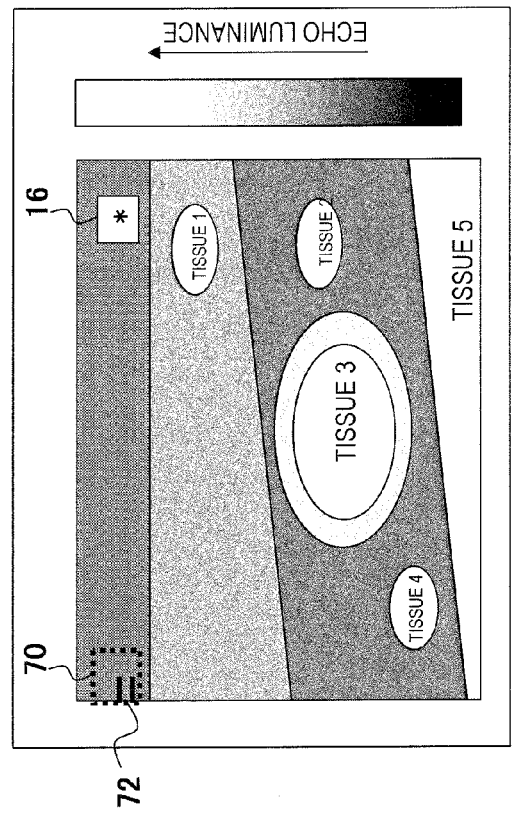
FIG. 9 shows a tomographic image of a reference deformable body including bar code, which is related to the present invention.
Figure 9:
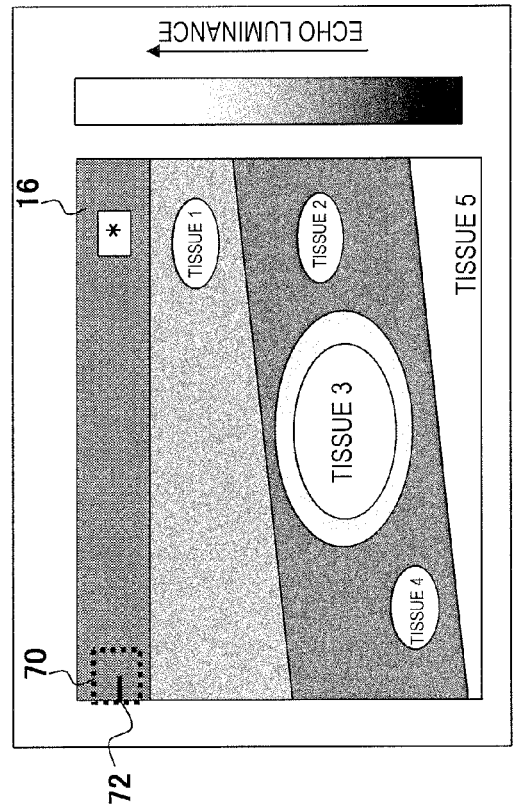

Also, as shown in FIG. 9, it is assumed that mark 72 formed by barcodes is appended to the side of reference deformable body 16. As shown in FIG. 9(*a*), in the case that reference deformable body 16 includes one strip of barcode, ID 40 of reference deformable body 16 is set as α. As shown in FIG. 9(*b*), in the case that reference deformable body 16 includes two strips of barcodes, ID 40 of reference deformable body 16 is set as β. The relationship between the number of strips in barcode and ID 40 of reference deformable body 16 is stored in memory 52. The echo luminance of barcode should be different from the echo luminance of reference deformable body 16. The array direction of the barcode is the major-axis direction or minor-axis direction of reference deformable body 16.

Image analyzing unit 60 analyzes the number of strips of barcode in reference deformable body 16 from the echo luminance of the elasticity image. Then type identifying unit 54 reads out and identifies ID 40 of reference deformable body 16 corresponding to the analyzed number of strips of barcode from memory 52.

While barcode is used as mark 72 here, a concave portion or notch may also be used. Also, by stretching a very thin string (for example, a fish line) inside of reference deformable body 16 along the minor-axis direction of reference deformable body 16, the information on the number of the strings or interval between the strips may be also used as mark 72.

Third Embodiment

Image Processing

The third embodiment will now be described referring to FIGS. 10 and 11. The difference from the first embodiment and the second embodiment is that image processing is executed by identifying the type of reference deformable unit 16.

Figure 10:
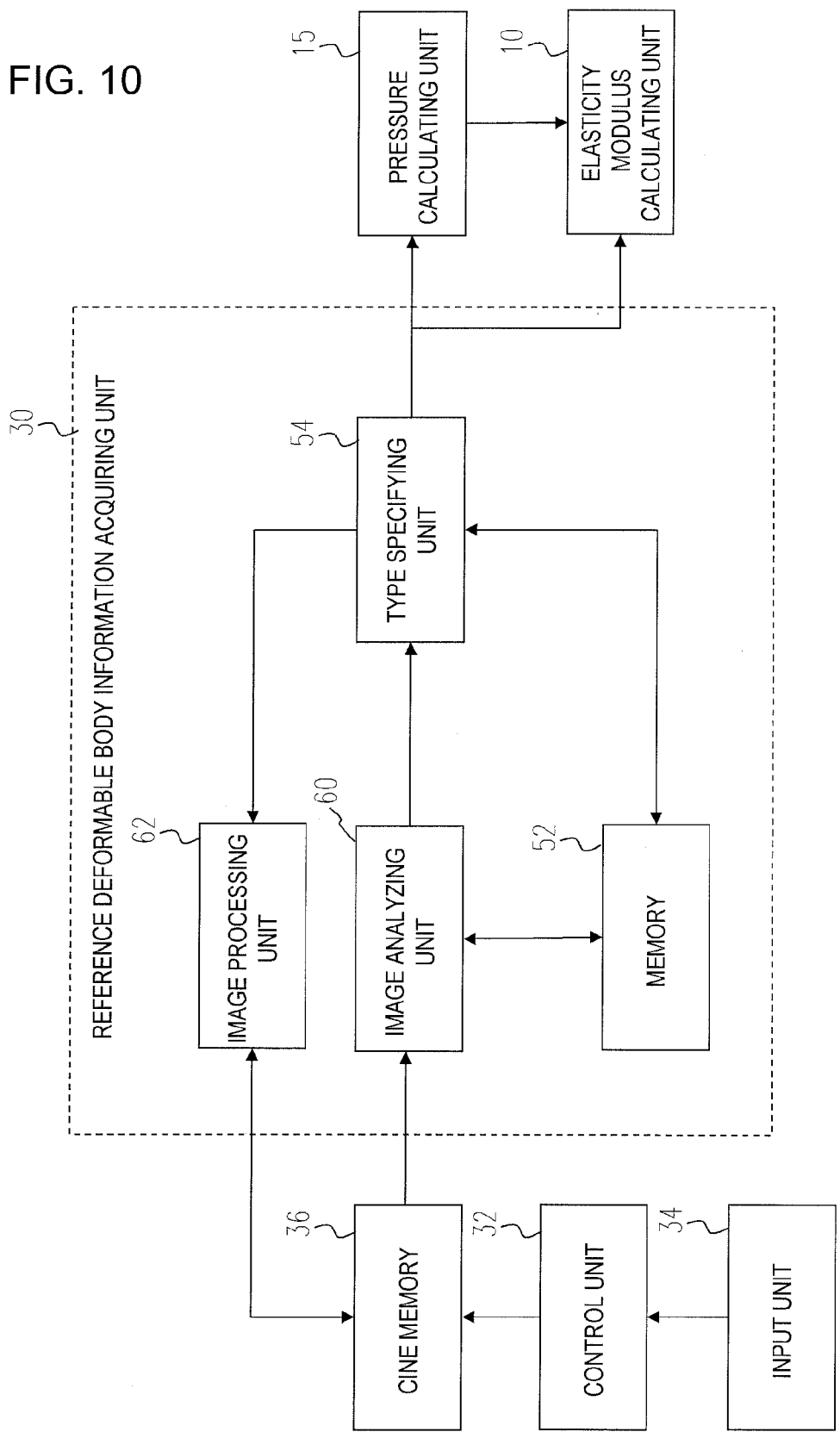
FIG. 10 shows the third embodiment of the present invention.

As shown in FIG. 10, reference deformable body information acquiring unit 30 has image processing unit 62 for executing image processing with respect to the tomographic image (or elasticity image) stored in cine memory 36, in addition to the above-described image analyzing unit 60, memory 52 and type identifying unit 54.

Type identifying unit 54 outputs ID 40 of reference deformable body 16 (includes thickness, elasticity characteristics, acoustic characteristics, kind of probe, etc.) to image processing unit 62. Image processing unit 62 detects thickness from ID 40.

Figure 11:
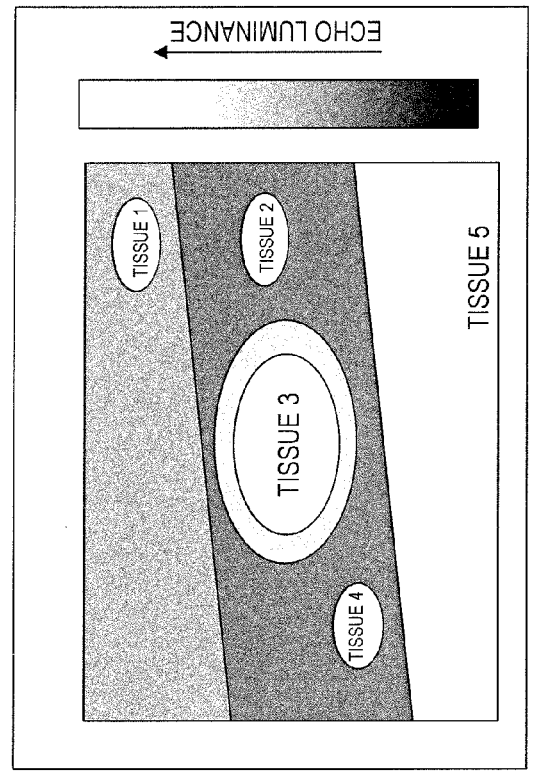
FIG. 11 shows tomographic images before and after receiving correction process.
Figure 11:
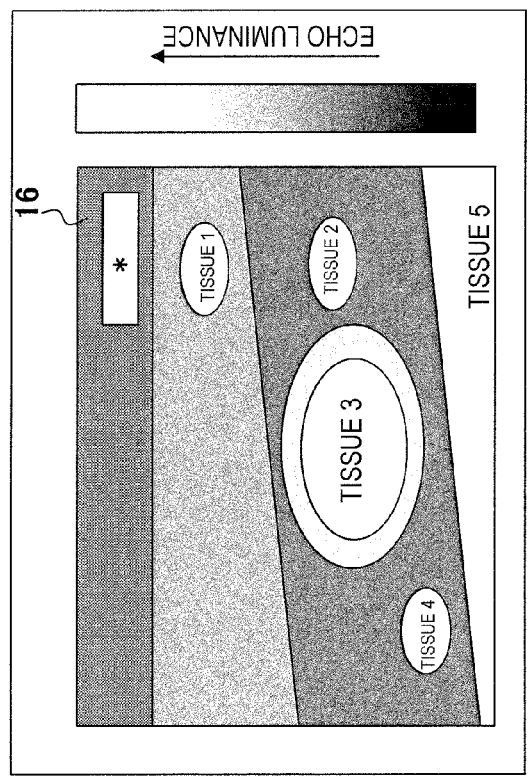

As shown in FIG. 11, image processing unit 62 shifts the tomographic image toward the upper direction (the side of ultrasonic probe 3) according to the "thickness" of reference deformable body 16 so as not to display reference deformable body 16. FIG. 11(*a*) shows the tomographic image before the correction, and FIG. 11(*b*) shows the tomographic image after the correction.

In concrete terms, as shown in Chart 1, if ID 40 identified in type identifying unit 54 is AAAA, the thickness of reference deformable body 16 is 8 mm. Image processing unit 62 loads the thickness information of the reference deformable body from type identifying unit 54, and shifts the tomographic image stored in cine memory 36 in the upper direction by 8 mm. If ID 40 is BAAA, the thickness of reference deformable unit 16 is 7 mm. Image processing unit 62 loads thickness information of the reference deformable body from type identifying unit 54, and shifts the tomographic image stored in cine memory 36 in the upper direction by 7 mm.

In this manner, as shown in FIG. 11(*b*), since reference deformable body 16 is not displayed on image display unit 14, it is possible to broaden the display region of tissue 5 in the deep portion.

Fourth Embodiment

Focus Only on the Thickness Portion

Here, the fourth embodiment will be described. The difference from the first embodiment~the third embodiment is that transmission and reception of ultrasonic waves is controlled by identifying ID 40 of reference deformable body 16.

In the present embodiment, though not shown in the diagram, reference deformable body information acquiring unit 30 is connected with ultrasonic-wave transmission/reception control circuit 1.

Type identifying unit 54 outputs ID 40 of reference deformable body 16 (includes thickness, elasticity characteristics, acoustic characteristics, kind of probe, etc.) to ultrasonic-wave transmission/reception control circuit 1. Ultrasonic-wave transmission/reception control circuit 1 detects "thickness" from ID 40. Then ultrasonic-wave transmission/reception control circuit 1 controls focus of the ultrasonic waves according to the thickness so that the ultrasonic waves will not be focused on reference deformable body 16.

In concrete terms, as shown in Chart 1, if ID 40 identified in type identifying unit 54 is AAAA, the thickness of reference deformable body 16 is 8 mm. Ultrasonic-wave transmission/reception circuit 1 loads the thickness information of the reference deformable body from type identifying unit 54, and controls transmission circuit 2 and receiving circuit 4 so that ultrasonic waves will be focused at the depth deeper than 8 mm to avoid ultrasonic waves from being focused on reference deformable body 16.

Accordingly, since ultrasonic waves are focused on tissues 1~5 of the object, image display unit 14 can display the tomographic image appropriately.

The invention claimed is:

1. An ultrasonic diagnostic apparatus comprising:

an ultrasonic probe including an ultrasonic transmitting/receiving surface;
a reference deformable body attached to the ultrasonic transmitting/receiving surface of the ultrasonic probe;
a tomographic image constructing unit configured to transmit/receive ultrasonic waves to/from an object to be examined via the reference deformable body, and generate a tomographic image based on RF signal frame data of a cross-sectional region of the object;
a storing unit configured to store a type of the reference deformable body corresponding to an ID of the reference deformable body;
an input unit configured to input the ID of the reference deformable body;
a type specifying unit configured to specify the type of the reference deformable body corresponding to the inputted ID; and
a display unit configured to display the tomographic image,
wherein said tomographic image constructing unit generates the tomographic image based on the specified type of the reference deformable body, and wherein the type of the reference deformable body includes at least one of thickness of the reference deformable body, elasticity characteristics of the reference deformable body including elasticity modulus, acoustic characteristics, scatterer concentration, and a kind of ultrasonic probe to be attached.

2. The ultrasonic diagnostic apparatus according to claim 1, wherein the display unit displays at least one of an ID of the reference deformable body which is identified in the type unit or type of the reference deformable body.

3. The ultrasonic diagnostic apparatus according to claim 1, wherein the ID is appended at least to one of the reference deformable body or the package thereof.

4. The ultrasonic diagnostic apparatus according to claim 1, wherein further comprising:
a pressure calculating unit configured to read out information on thickness and elasticity modulus from among the types of the reference deformable body stored in the type specifying unit, and calculate the pressure applied on the reference deformable body;
a strain calculating unit configured to calculate strain of a tissue in the cross-sectional region based on the RF signal frame data; and
an elasticity modulus calculating unit configured to calculate elasticity modulus of the tissue based on the calculated pressure and strain.

5. The ultrasonic diagnostic apparatus according to claim 4, wherein the pressure calculating unit calculates the pressure applied to the reference deformable body based on the strain and the elasticity modulus obtained from the thickness and displacement of the reference deformable body.

6. The ultrasonic diagnostic apparatus according to claim 4, further comprising an elasticity image constructing unit configured to generate an elasticity image based on the elasticity modulus of a tissue calculated by the elasticity modulus calculating unit.

7. An ultrasonic diagnostic apparatus comprising:
an ultrasonic probe including an ultrasonic transmitting/receiving surface;
a reference deformable body attached to the ultrasonic transmitting/receiving surface of the ultrasonic probe;
a tomographic image constructing unit configured to transmit/receive ultrasonic waves to/from an object to be examined via the reference deformable body, and generate a tomographic image based on RF signal frame data of a cross-sectional region of the object;
an image analyzing unit configured to analyze feature quantity of the reference deformable body in the tomographic image;
a storing unit configured to store a type of the reference deformable body corresponding to the analyzed feature quantity of the reference deformable body;
a type specifying unit configured to specify a type of the reference deformable body, and identify the type of the reference deformable body; and
a display unit configured to display the tomographic image,
wherein said tomographic image constructing unit generates the tomographic image based on the specified type of the reference deformable body, and wherein the type of the reference deformable body includes at least one of thickness of the reference deformable body, elasticity characteristics of the reference deformable body including elasticity modulus, acoustic characteristics, scatterer concentration, and a kind of ultrasonic probe to be attached.

8. The ultrasonic diagnostic apparatus according to claim 7, wherein:
the feature quantity is the average value of an echo luminance in the tomographic image; and
the type specifying unit identifies the type of the reference deformable body based on an average value of the echo luminance in a newly-obtained tomographic image.

9. The ultrasonic diagnostic apparatus according to claim 7, wherein:
the feature quantity is an echo luminance of the scatterer included in the reference deformable body; and
the type specifying unit identifies the type of the reference deformable body based on the pattern, size or form of a scatterer in a newly-obtained tomographic image.

10. The ultrasonic diagnostic apparatus according to claim 7, wherein:
the feature quantity is a form of the reference deformable body or a feature substance included in the reference deformable body, and
the type specifying unit identifies the type of the reference deformable body based on the form or feature substance of the reference deformable body in a newly-obtained tomographic image.

11. The ultrasonic diagnostic apparatus according to claim 1, further comprising an image processing unit configured to shift a tomographic image or elasticity image toward the side of the ultrasonic probe, in accordance with a thickness of the reference deformable body identified by the type specifying unit.

12. The ultrasonic diagnostic apparatus according to claim 1, further comprising an ultrasonic-wave transmission/reception control unit configured to control focus of the ultrasonic wave so that the ultrasonic wave is not focused on the reference deformable body, in accordance with a thickness of the reference deformable body identified by the type specifying unit.

13. An ultrasonic diagnostic method using an ultrasonic diagnostic apparatus comprising the steps:
storing a plurality of types of reference deformable bodies and a corresponding ID for each reference deformable body;
inputting an ID corresponding to a current reference deformable body;
specifying a type of the current reference deformable body corresponding to the input ID;

pressing an ultrasonic probe, having the current reference deformable body attached to an ultrasonic transmitting/receiving surface thereof, against an object to be examined;

transmitting/receiving ultrasonic waves to/from the object to be examined via the reference deformable body;

generating a tomographic image based on both RF signal frame data of a cross-sectional region of the object to be examined and the specified type of the current reference deformable body; and displaying the tomographic image on a display unit, wherein the type of the reference deformable body includes at least one of thickness of the reference deformable body, elasticity characteristics of the reference deformable body including elasticity modulus, acoustic characteristics, scatterer concentration, and a kind of ultrasonic probe to be attached.

14. The ultrasonic diagnostic apparatus according to claim 7,
wherein the storing unit is configured to store relationship between an ID appended to the reference deformable body and the type of the reference deformable body; and
further comprising a type identifying unit configured to read out the type of the reference deformable body corresponding to the ID of the reference deformable body which is attached to the ultrasonic probe, and identify the type of the reference deformable body.

15. The ultrasonic diagnostic apparatus according to claim 7, further comprising:
a pressure calculating unit configured to read out information on thickness and elasticity modulus from among the types of the reference deformable body stored in the type identifying unit, and calculate the pressure applied on the reference deformable body;
a strain calculating unit configured to calculate strain of a tissue in the cross-sectional region based on the RF signal frame data; and
an elasticity modulus calculating unit configured to calculated elasticity modulus of the tissue based on the calculated pressure and strain.

16. The ultrasonic diagnostic apparatus according to claim 15, wherein the pressure calculating unit calculates the pressure applied to the reference deformable body based on the strain and the elasticity modulus obtained from the thickness and displacement of the reference deformable body.

17. The ultrasonic diagnostic apparatus according to claim 15, further comprising an elasticity image constructing unit configured to generate an elasticity image based on the elasticity modulus of a tissue calculated by the elasticity modulus calculating unit.

18. The ultrasonic diagnostic apparatus according to claim 7, further comprising an image processing unit configured to shift a tomographic image or elasticity image toward the side of the ultrasonic probe, in accordance with the thickness of the reference deformable body identified by the type identifying unit.

19. The ultrasonic diagnostic apparatus according to claim 7, further comprising an ultrasonic-wave transmission/reception control unit configured to control focus of the ultrasonic wave so that the ultrasonic wave is not focused on the reference deformable body, in accordance with the thickness of the reference deformable body identified by the type identifying unit.

\* \* \* \* \*